United States Patent [19]

Damato

[11] Patent Number: 5,886,770
[45] Date of Patent: Mar. 23, 1999

[54] DEVICE FOR USE IN THE EXAMINATION OF THE VISUAL FIELD OF A SUBJECT

[75] Inventor: Bertil Eric Damato, Cheshire, United Kingdom

[73] Assignee: University Court of the University of Glasgow, Glasgow, Scotland, United Kingdom

[21] Appl. No.: 619,471

[22] PCT Filed: Sep. 22, 1994

[86] PCT No.: PCT/GB94/02066

§ 371 Date: Mar. 22, 1996

§ 102(e) Date: Mar. 22, 1996

[87] PCT Pub. No.: WO95/08290

PCT Pub. Date: Mar. 30, 1995

[30] Foreign Application Priority Data

Sep. 22, 1993 [GB] United Kingdom .................... 9319588

[51] Int. Cl.[6] ...................................................... A61B 3/02
[52] U.S. Cl. ........................... 351/237; 351/222; 351/246
[58] Field of Search .................................... 351/239, 237, 351/246, 238, 222, 243, 223

[56] References Cited

U.S. PATENT DOCUMENTS 2,576,358  11/1951  Pritikin .
4,737,024   4/1988  Damato ................................... 351/224
4,995,717   2/1991  Damato ................................... 351/224
5,061,059  10/1991  Horn ....................................... 651/232

FOREIGN PATENT DOCUMENTS 0164358  12/1985  United Kingdom .
2247087   2/1992  United Kingdom .
2264366   9/1993  United Kingdom .

Primary Examiner—Hung Xuan Dang
Attorney, Agent, or Firm—Jefferson Perkins Foley & Lardner

[57] ABSTRACT

A visual field test device (10) is disclosed which allows a larger area of the visual field to be examined and allows use of the device for testing for diseases of the eye and brain, for example, glaucoma. The device consists of a chart (12) which has visual target patterns (13) for the left and right eyes and which is foldable about fold line (45) so that the visual targets are on front and rear surfaces of the device (10). Each visual target consists of about 60 fixation targets (14), represented by sequential numbers, arranged to spiral outwards along lines (16) to facilitate use by test subjects. A plurality of test stimuli (21) are located on a rotatable disc (18) and the chart (12) has a central aperture (20) through which a selected test stimuli (21) can be viewed. Different test stimuli can be used as required and in one embodiment a moveable cover (22) can be used to obscure the test stimuli. The test subject follows the fixation targets (14) sequentially and announces, for each fixation target, whether the test stimuli can be seen. This allows a map of the subject's visual field to be created, for each eye to ensure that the eye examination is more foolproof and allows easier variation in stimulus size and intensity.

33 Claims, 4 Drawing Sheets

DEVICE FOR USE IN THE EXAMINATION OF THE VISUAL FIELD OF A SUBJECT

TECHNICAL FIELD OF THE INVENTION

This invention relates to visual field examinations and is concerned with a device for use in such visual field examinations or multifixation campimetry, that is, a method of testing for diseases of the eye and brain, for example glaucoma, in which the eye under examination is encouraged to move in a controlled manner in order to position a fixed central test stimulus at known positions in the visual field. The invention also relates to a method of using the device.

DESCRIPTION OF THE RELATED ART

In our European Patent No. 164,981 there is disclosed an oculo-perimetric device, which is relatively cheap and which can be used by a patient without skilled assistance or by an examiner. With this device eye movements are controlled by a series of fixation targets positioned around a fixed central test stimulus in the form of a reference target spot, and the device consists of an extended area visual target having a large plurality of generally regularly, angularly and/or radially spaced apart individual target elements disposed around the central reference target spot across substantially the whole of the area within a predetermined radial separation from said reference target spot. The individual target elements are a predetermined pattern of numbers arranged so as to define a visually discernible predetermined sequence for fixing of an eye of the subject, in use of the device, on successive adjacent individual target elements, said central reference target element being formed and arranged so as to be visually more prominent than said individual target elements. The eye is fixed on each number in turn and, should the reference target element in the centre not be visible out of the corner of the eye, then a potential defect in the field of vision is likely. In this way a map of defective areas in the patient's field of vision can be drawn up. One difficulty with this test card is that it is required to be placed at a correct distance from the patient's eye and in the correct side-to-side and up-down orientation. The correct distance from the subject's eye is achieved by means of a rigid side arm, which is pivotably attached to one side of the chart at one end and to an eye-occluder at the other end. In the disclosed method, this was also achieved by moving the test card to and from the patient, from side to side, and up and down with the eye fixed on an 'L' or 'R' marking (for left or right eye respectively) until the central target spot disappears in the patient's blind spot.

Whilst in theory this method is appropriate, in practice the number of possible orientations of the card makes correct positioning difficult for the unskilled user and may thus result in incorrect results being obtained.

It is an object of the present invention to obviate or mitigate at least one of the aforementioned disadvantages.

It is a further object of the present invention to provide an improved visual field examining device which has greater and variable sensitivity compared with the aforementioned device, which makes it easier for an examiner to assess the subject's cooperation, and which allows a larger area of the visual field to be examined, and also the device may be used for purposes other than the detection of glaucoma.

SUMMARY OF THE INVENTION

Thus, in accordance with one aspect of the present invention, there is provided a device for use in the examination of the visual field of a subject, which device comprises a visual target pattern having a plurality of spaced individual fixation targets disposed in a predetermined configuration around a substantially central test stimulus and across substantially the whole of the visual target pattern, each individual fixation target incorporating sequence indicating means so as to define a visually discernible predetermined sequence for fixing of an eye of the subject, in use of the device, on selected individual fixation targets, the arrangement being such that, in use, actuation of the central test stimulus causes a preselected test stimuli to be presented to the subject under test.

Conveniently, the central test stimulus is variable. Alternatively it may be continuous. Preferably, the test stimulus may be a moveable element or a light source. The light source may be continuous or flickering and the intensity of the light source can be varied using active means such as a rheostat or passive means such as a filter. A filter may also be used over black spots, for example. Conveniently, the central variable test stimulus comprises a moveable element which has a plurality of spaced apart test stimuli which can be the same or different. The moveable element may be moved only to position the stimulus in the window, and that thereafter a shutter will be opened and closed so that the now immobile stimulus will appear and disappear. The shutter may be an arc, rotating disc, slide-rule or even a graduated filter.

Preferably, the moveable element is a rotatable disc. Conveniently, four different test stimuli are located on the disc although more or less stimuli can be used. The disc does not protrude from the edge of the device.

Conveniently, the test stimulus is more visually prominent than the fixation targets if the test stimulus is constantly exposed. Preferably, when the test stimulus is presented intermittently the test stimulus may be less visually prominent than the fixation targets. The test stimuli can be lighter, making the test more sensitive; and the fixation targets may be darker, so that they are discernable to patients with reduced visual acuity.

The different test stimuli may differ, for example, in size, shape, contrast or colour. For instance, the test stimulus may take the form of a spot, wedge or line which can change in size and/or contrast as the disc is rotated. The test stimuli may be dark stimuli on a light background or light stimuli on a dark background. The disc has diameters and contrasts printed near the edge so that they appear in a notch on the chart when the appropriate stimulus appears in the central window. Arrows along the edge of the chart also indicate which way to rotate the disc to make the stimulus darker or smaller or darker or brighter. To prevent this information being revealed to the patients the notch may be covered by a flap.

The individual fixation targets may be successively arranged and successive targets may be adjacent.

The fixation targets may, in one embodiment of the invention, be in a substantially regularly and generally spirally-arranged configuration around the central test stimulus. The fixation targets may be numbers, letter or symbols. The numbers may be semi-randomised (e.g. ascending only: 1,3,4,6,9,12,13 etc.). All numbers need not be examined and intermediate points in blank areas of the visual target may be examined, if necessary. Alternatively, the fixation targets may be arranged in a more physiological pattern in which the fixation targets are not in a generally regular spiral around the test stimulus, but instead are arranged in a distorted spiral in positions which are substantially equi-sensitive with respect to the stimulus.

If desired, the visual target may have printed thereon a faint grid identifying the various targets in the visual field, to facilitate localisation of intervening points.

The device of the invention enables different test stimuli to be readily and easily presented to the subject under examination in a more reliable fashion, as well as the speed of the examination to be increased, thereby making it possible to increase the number of targets examined.

BRIEF DESCRIPTION OF THE DRAWINGS

These and other aspects of the present invention will become apparent from the following description when taken in combination with the accompanying drawings in which.

DETAILED DESCRIPTION OF THE INVENTION

Figure 1:
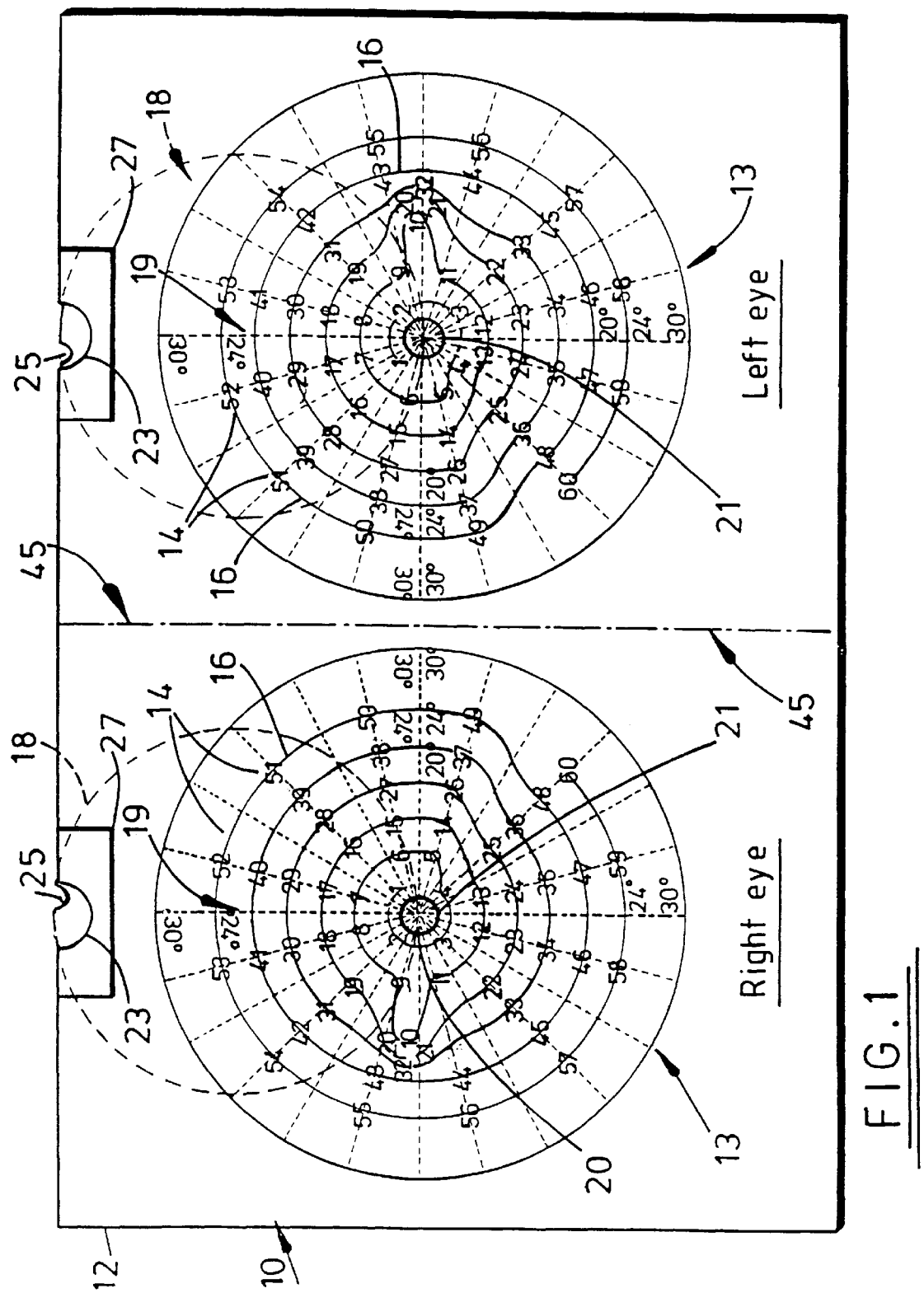
FIG. 1 depicts a first embodiment of a developed view of a visual target device in accordance with the present invention but without the arm and occluder patch.
Figure 2:
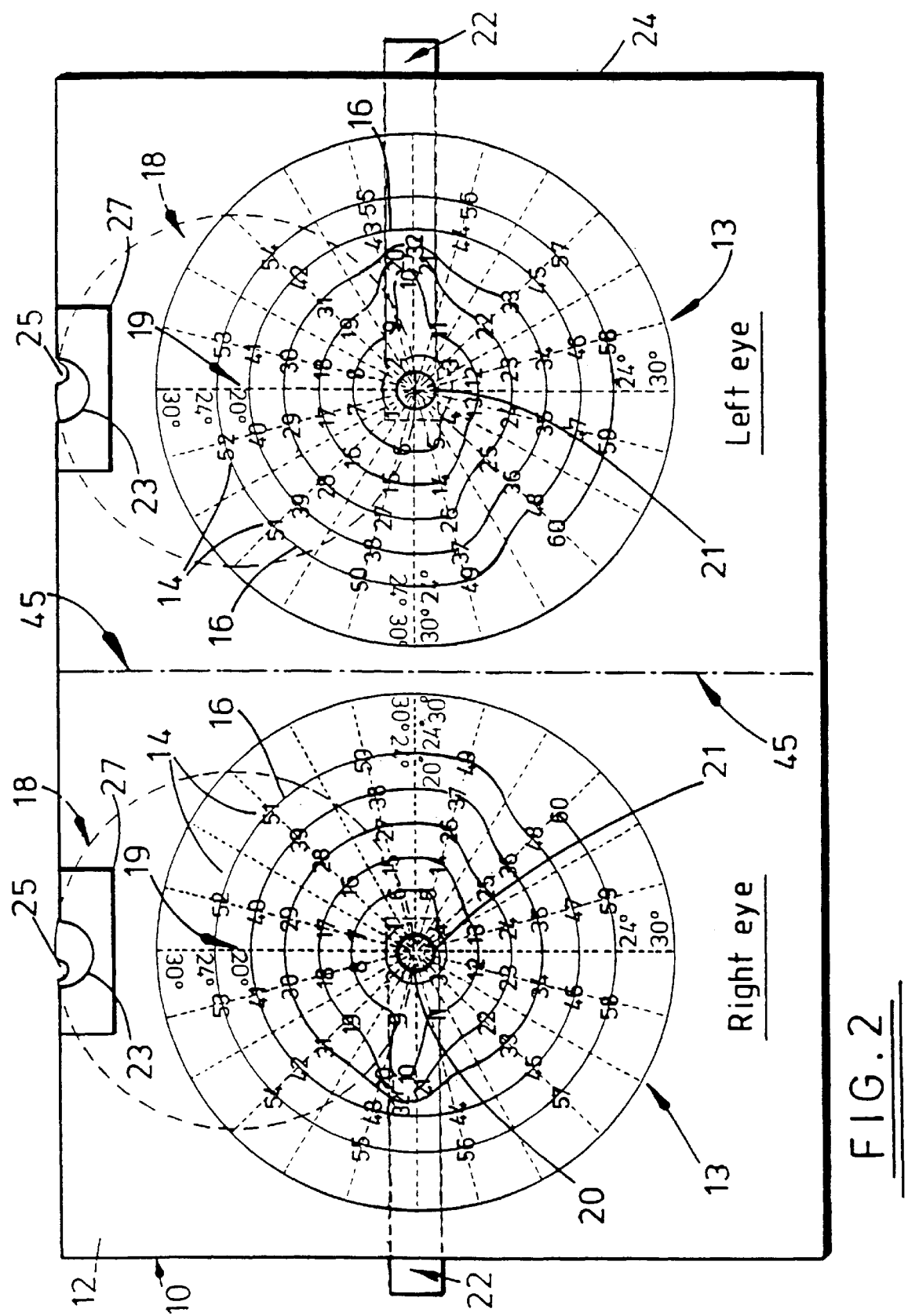
FIG. 2 is a second embodiment of a visual target device similar to that shown in FIG. 1.

The device shown in FIG. 1, generally indicated by reference numeral 10, takes the form of a cardboard chart 12 having printed thereon a visual target pattern 13 for the left and right eyes comprising some 60 individual fixation targets 14 identified by sequential numbers in the central 24 degree field, with the facility to test quadrants to 30 degrees. The target numbers 14 are linked by lines 16 for the assistance of patients/subjects in finding the next number, this being of particular benefit for patients who are unable to read and spiral outwards from 4 degrees so that, if desired, the examiner can commence the test with a weak stimulus and thereafter progress to stronger stimuli as more peripheral target numbers are examined. The spiral arrangement of the target numbers also makes it easier for the examiner to omit the testing of paracentral or peripheral target numbers, if it becomes necessary to abbreviate the examination. In FIGS. 1 and 2 it will be seen that fixation point numbers 10, 20, 21 and 32 form a cluster on both right and left eye visual field patterns and these numbers correspond to the location of the subject's blindspots for respective eyes. Therefore, when the subject looks at one or more of these numbered fixation points any test stimulus presented should not be seen.

It will be seen that the target numbers are distributed in a substantially regular fashion at intervals of 4 degrees radially and 24 degrees meridionally, so that if additional targets need to be examined, these can easily be localised in the visual field. It will be seen that the circle goes to 30°, because too many numbers would be intimidating. Any number of intervening targets (or if necessary all the targets) can easily be examined using a moveable hand-held pointer (not shown) as a fixation target. The moveable fixation target may comprise, for example, a circle or cross on the end of a wand, this being of particular use for patients who cannot see the target numbers. It is also possible to employ a hand-held, rigid or flexible wand which can be moved, by the patient under examination, in a manner such that the tip of the wand, which may or may not include a target, is superimposed on the fixation target. This is particularly useful for dealing with patients who have insufficient self-control to keep looking at a number target as the stimulus is presented.

The visual target 10 shown in FIG. 1 allows the pattern of visual field loss to be determined so that differential diagnosis is possible. A 26-point chart (not shown) is used to screen for glaucoma and is designed to be used by non-experts. It examines only those points that are most important and is as simple, or minimalist as possible. For example, if any point is missed more than once, the result is abnormal. However, the target 10 may be useful to detecting glaucoma, but also for detecting other diseases of the eyes and brain, making it of more use to neurologists and general physicians. The 60 point chart uses a different criteria for abnormality; a single missed point does not necessarily mean the result is abnormal because the examiner is looking for asymmetries between the two eyes and between different quadrants in the same field.

Figure 3:
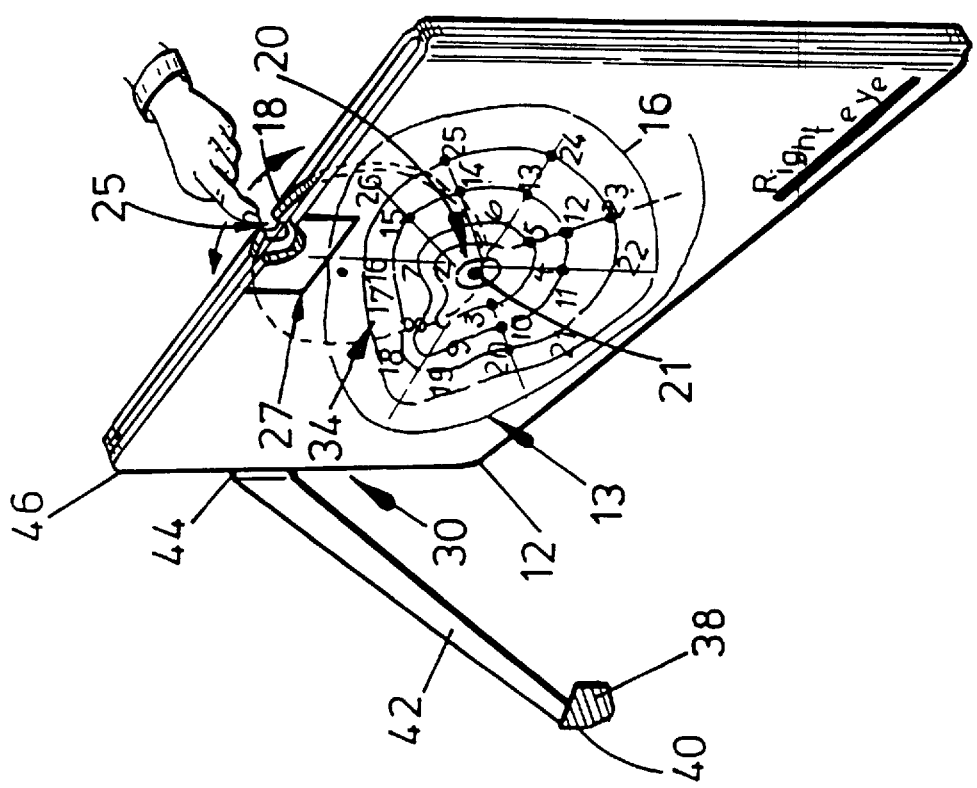
FIG. 3 depicts a folded visual target device in accordance with a preferred embodiment of the present invention including an arm and occluder patch.

In accordance with one embodiment of the invention shown in FIG. 1, a test stimuli-bearing disc 18 (shown in broken outline) is rotatably mounted by axle 19 to the visual target chart 10 when folded as shown in FIG. 3. Each face is provided with a central aperture or window 20 through which the various test stimuli 21 (only one of which is shown in the interests of clarity) can be viewed by the test subject. The test stimuli 21 can be spaced apart on the disc, so as to enable either one of the stimuli, or a blank space, to be presented to the patient.

The window 20 is slightly longer than the largest stimulus so that the examiner does not need to be too careful about rotating the disc. The spaces between the stimuli allow the window to be empty. A notch 23 is formed on the margin of the chart and has a width such that, when the examiner's finger moves from one side of the notch to the other, one stimulus in the central window 20 is replaced by the next stimulus. The edge of the disc 18 has notches 25 corresponding to where the examiner's finger should be placed. A flap 27 hinged along the upper edge of the device 10 can be used to hide the examiner's finger so that the subject cannot anticipate movement of the test stimulus.

In an alternative embodiment shown in FIG. 2, the test stimuli can be positioned close together on the disc 18 to enable one stimulus to be replaced immediately by another, with a moveable cover 22 being provided to enable the stimuli to be covered up when required by the examiner. The moveable cover 22 (shown in broken outline) may take the form of a slidable elongate rectangular member which can be operated by means of an exposed end extending from the edge 24 of the target chart 12, so as either to cover up or reveal each test stimulus. This slidable member may be white and opaque, or it may be a neutral density filter the transparency of which varies along its length.

In a preferred embodiment of the invention, the target chart 30 is double-sided, with one side bearing a target pattern suitable for the right eye and the other side bearing a target pattern for the left eye, and with the test stimuli-bearing disc being sandwiched between the two sides of the test chart as shown in FIG. 3, there being a cut-out window 21 in the central area 34 of the chart through which the various test stimuli on the rotatable disc 18 can be viewed. Notches 23 are formed in the upper margins of both sides of the test chart so as to expose a portion of the disc 18, whereby the examiner can cause the disc 18 to rotate in either direction by appropriate movement of a finger placed on the exposed edge or notch 25 of the disc unseen by the subject/patient when flap 27 is used. As the disc is rotated, the test subject can be asked to indicate when the stimulus appears or disappears. If the subject cannot see the stimulus, a different, e.g. larger or more intense, stimulus can be presented to the subject by simple rotation of the disc. The chart has round corners to avoid injury to the subject and examiner and avoids 'dog-earing' of the device. The edge of the disc does not protrude from the side of the chart to prevent damage. Three of the four edges are sealed (at present) so that to replace a disc the chart is opened like a purse. In FIG. 3 the disc can be replaced from the top. The axle 19 of the disc is positioned so that it does not interfere with any of the numbers and spacers (not shown) are disposed between the front and back to ensure free disc rotation.

Advantageously, the disc 18 is removably attached to the chart 12, so that different discs can be interchanged if desired, thereby making it possible to have further variations in, e.g. the size, contrast or colour, of the stimuli.

The target chart and rotatable disc may advantageously be made from cardboard, or from a more durable material, for example a plastics material.

In the preferred embodiment of the invention shown in FIG. 3, an eye occluder 38 is attached, by means of a spiral hinge 40, to a rigid side-arm 42 which itself is attached by a spiral hinge 44 to a vertical side 46 of the test chart 12, which ensures an accurate and repeatable test position for both sides of the chart, if the subject's eye is directly in front of the centre of the test chart. This has the advantage that if the wrong eye is covered, the subject cannot see the chart with either eye. The arm may be hinged at the lower edge of the chart so it could be moved from eye to eye. The eye occluder 38 may be formed from cardboard or from a suitable plastics material, the latter being easier to sterilise.

It will be understood that various modifications may be made to the invention hereinbefore described without departing from the scope of the invention. For example, the fixation target numbers may be replaced by letters, icons or the like and the radial and circumferential spacing may be varied as required. The numbered fixation targets may be 'coded' for different diseases, for example one set for glaucoma and another set for a different disease. The structure of the chart may be a plastic material folded about a fold axis with right and left eye charts on either side of the fold so that when the chart is folded the left and right eye diagrams appear on obverse and reverse sides. The chart can be mounted on an easel or the like to permit it to be self-supporting on a desk. It will also be understood that the fixation targets and test stimuli may be represented by changeable light sources such as LEDs, LCDs or the like.

Figure 4:
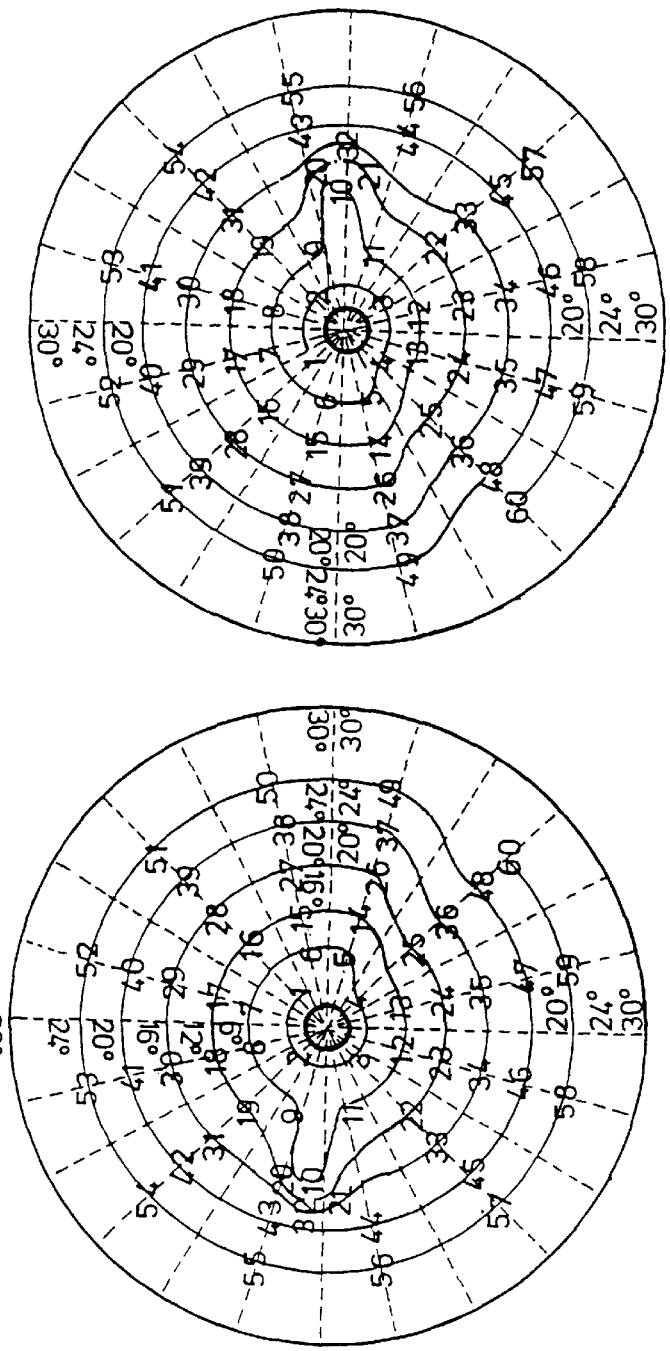
FIG. 4 is a view of a record/interpretation sheet for use with the devices shown in FIGS. 1 to 3.

The extended area visual target is capable of carrying one or more sheets each displaying an appropriate test grid for testing a particular facet of the performance of the field of vision in a detachable way. In the same way, a pad of tear-off sheets could be mounted on the visual target for once-only use. FIG. 4 shows a visual test/interpretation chart for use with the devices shown in FIG. 4 for use with the left and right eyes. Data is recorded in one orientation and then the chart is inverted to interpret the results.

For further convenience, a retaining means, such as a loop or clip (not shown), could be provided on the device for holding a pen, pencil or other marking means. If desired, the device could be provided with a stand for supporting on a desk etc. or with wall mounting means (such as holes, adhesive means etc.) for hanging on a wall. The upper edge of the chart is straight but may be made rounded to allow an examiner to look over the top of the chart. The pattern of target elements is usually arranged so as to sample the whole of the central part of the field of vision of the subject. For simplicity, the target elements are usually arranged consecutively such that the eye can easily travel from one to the next, and usually they are joined by lines to form a spiral which make tracing the pattern more easy. Other patterns of reference target elements such as zig-zags or star-shapes could be employed for particular purposes to follow 'contour lines' or 'isopter' correlating retinal sensitivity with eccentricity. It would also be possible to use other target elements such as hollow circles, squares, triangles etc. which are filled in or left blank by the subject. A grid pattern of lines might equally be used, the subject entering the result in the appropriate box on the grid.

It will be appreciated that the test stimulus can be variable or continuous, for example a line getting darker compared to separate spaced test stimuli. Also, sequence indicating means can be numbers, letters, symbols or the contour of the line.

The central aperture is not necessarily central. The aperture is wider above than below so that the sides face upwards. The stimulus is also further from the upper edge of the window than the lower edge to minimise shadows cast on the disc by the edges of the aperture, which may be bevelled.

It will be appreciated that the device in accordance with an embodiment of the invention can be used by subject/ patients themselves to administer self-testing as well as by an examiner. The instructions for use by an examiner are given below although similar instructions can be given for self-testing.

Instructions for Use by an Examiner

This visual field test has been designed to allow examination of the visual field when more sophisticated methods are impractical. It uses the subject's/patient's eye movements to position a fixed test stimulus at known points in the visual field, using a series of fixation targets to alter the direction of gaze in a precise manner.

The chart is attached to an eye-cover by a side arm, which ensures accurate and repeatable testing position.

The fixation targets are numbered to guide eye movements and to simplify recording of the results. They are blue to be differentiated easily from the black test stimulus.

The lines linking the numbers are for the benefit of patients who cannot read.

The chart has found interchangeable stimuli, 1 mm, 2 mm, 4 mm and 8 mm in diameter. The stimuli are printed on a disk inside the chart and appear individually in a central window when the disk is rotated. This 'dial-a-dot' mechanism makes it convenient for the examiner to present a selected stimulus intermittently so as to prevent the patient from guessing.

The stimuli are black on a white background to reduce the need for uniform lighting conditions.

The blindspot is examined surreptitiously by numbers '10', '20', '21' and '32'. This allows the examiner to (i) check that the test is being performed correctly, (ii) judge the patient's reliability, and (iii) teach the patient the principles of the examination.

The record sheet (FIG. 4) has a miniature version of the test grid for each eye to allow documentation of the number associated with disappearance of the stimulus.

Preparation for the Examination

The patient should be comfortably seated at a desk, wearing glasses or contact lenses if necessary.

Ensure that the room lighting is adequate and shade any on-coming bright light that might dazzle the patient.

Position yourself in front of the patient to observe both eyes.

Examination of the Right Eye

For hygienic reasons, wrap the eye-cover in tissue paper.

Place the eye-cover in the patient's left hand and the ridge edge of the chart in the patient's right hand. Ask the patient to cover the left eye by holding the eye-cover, folded inwards, against the closed eyelid or, if glasses are being worn, against the spectacle lens.

Check that neither the patient's head nor the chart are tilted sideways. If possible, rest the lower edge of the chart on the desk. Adjust the position of the chart so that it faces the patient squarely, with the stimulus 13 ins (33 cm) directly in front of the right eye. You can tilt the chart backwards and forwards according to the height of the patient.

Do not let any shadows fall on the test grid.

Avoid any lengthy instructions, which cause delay and which are often misunderstood; a few brief introductory remarks should be adequate.

Draw attention to the window on the chart and dial the disc from side to side so that the patient can see the 1 mm stimulus appearing and disappearing. Then tell the patient to look at the number '1' and not to look at the stimulus again.

Ask the patient to say 'yes' or 'come' when the stimulus is seen and 'no' or 'gone' when the stimulus is no longer seen and then rotate the disc slowly so that the stimulus appears and disappears in the central window.

Avoid giving any clues (e.g. noise, sudden movement etc.) and ensure that the patient's responses coincide precisely with the appearance or disappearance of the stimulus. You can see when the stimulus appears and disappears by glancing at the window on your side of the chart. Watch the patient closely at all times to check that the patient does not look away from the number and that the fellow eye is well covered.

Start with the smallest (1 mm) stimulus. If this is not see, then repeat the procedure one more time with the same stimulus. If the small stimulus is missed a second time, then repeat the examination with progressively larger stimuli.

When you have finished examining the first point, move to the next number on the chart and repeat the procedure in exactly the same way.

When the stimulus is not seen because it falls within the blindspot, you do not need to re-examine that point with larger stimuli. It will probably be helpful to reassure the patient by saying 'Well Done! You have just found your normal blindspot, which is present in every eye.'

Examination of the Left Eye

Turn the chart over and ask the patient to hold the patch against the closed right eye with the right hand, and the left edge of the chart with the left hand.

Ensure that the test grid is still free of shadows.

Documentation of the Results

If a number is associated with non-awareness of the stimulus, the corresponding number on the record sheet should be marked with the symbol appropriate for that stimulus, following to the guidelines on the record sheet.

Interpretation of the Results

Invert the record sheet at the end of the examination to asses the results.

The result is abnormal if there is any asymmetry between the two eyes or between different quadrants of the same eye.

The cover-uncover technique facilitated by the rotatable stimuli disc 18 of the invention enables assessment of the subject's ability to detect change in the visual field rather than awareness of a fixed stimulus at different points in the visual field. This has several advantages; firstly, any shadows cast on the disc by the margins of the window should be less troublesome; secondly, the fixation targets can be printed in a darker colour so as to be more legible, and thirdly, the intermittent stimulus presentation makes it possible to use low contrast stimuli instead of black stimuli, which favours peripheral contrast sensitivity measurement which is know to be superior to central contrast sensitivity testing in the detection of glaucomatous optic nerve damage.

I claim:

1. A device for use in the examination of the visual field of a subject, which device comprises a visual target pattern having a plurality of spaced individual fixation targets disposed in a predetermined configuration around a substantially central test stimulus and across substantially the whole of a visual target pattern, each individual fixation target incorporating sequence indicating means so as to define a visually discernible predetermined sequence for fixing of an eye of the subject, in use of the device, on selected individual fixation targets characterised by means for selectively actuating the central test stimulus during use so that the central test stimulus can be made visible or invisible to the subject under test.

2. A device as claimed in claim 1 wherein said central test stimulus is more visually prominent than the fixation targets when said central test stimulus is exposed.

3. A device as claimed in claim 1 wherein said central test stimulus is less visually prominent than the fixation targets when said central test stimulus is exposed.

4. A device as claimed in claim 1 wherein said means for selectively actuating said central test stimulus is a moveable element.

5. A device as claimed in claim 4 wherein said moveable element is a rotatable disc having printed thereon one or more test stimuli which may be presented to the subject under test as the central test stimulus.

6. A device as claimed in claim 5 wherein said means for selectively actuating said central test stimulus is a rotatable disc having printed thereon a plurality of test stimuli, one or more of which may be selected to be presented to the subject under test as the central test stimulus; said disc being rotatably attached to the rear of the visual target, said visual target being provided with a central aperture through which selected test stimuli may be viewed by the subject under test.

7. A device as claimed in claim 6 wherein the test stimuli are spaced apart on the disc so as to enable a selected stimulus, or a blank space, to be presented to the subject.

8. A device as claimed in claim 6 wherein the test stimuli are positioned close together on the disc to enable one stimulus to be replaced immediately by another stimulus; said device being further provided with a moveable cover allowing the stimuli to be covered up when required by the examiner.

9. A device as claimed in claim 6 wherein the test stimuli are positioned close together in the disc to enable one stimulus to be replaced immediately by another stimulus; said device being further provided with a moveable cover, said cover being in the form of a slidable member which is operable by means of an exposed end extending from the edge of the target chart so as to cover up or reveal each test stimulus.

10. A device as claimed in claim 6 wherein the test stimuli are positioned close together on the disc to enable one stimulus to be replaced immediately by another stimulus; said device being further provided with a moveable cover; said cover being in the form of a slidable member which is white or opaque or a neutral density filter, the transparency of which varies along its length, said slidable member being operable by means of an exposed end extending from the edge of the target chart so as to cover up or reveal each test stimulus.

11. A device as claimed in claim 1 wherein said central test stimulus is a light source.

12. A device as claimed in claim 1 wherein said means for selectively actuating said central test stimulus is a moveable element having a plurality of spaced test stimuli which are different.

13. A device as claimed in claim 12 wherein said central test stimuli differ in size, shape, contrast or colour.

14. A device as claimed in claim 12 wherein said means for selectively actuating said central test stimulus is a rotatable disc, and wherein said test stimulus is in the form of a spot, wedge or line which changes in size as said disc is rotated.

15. A device as claimed in claim 12 wherein said means for selectively actuating said central test stimulus is a rotatable disc, and wherein said test stimulus is in the form of a spot, wedge or line which changes in contrast as said disc is rotated.

16. A device as claimed claim 12 wherein the test stimuli include a dark stimulus on a light background and a light stimulus on a dark background.

17. A device as claimed in claim 12 which comprises a double-sided chart with one side of said double-sided chart bearing a visual target pattern suitable for the right eye and the other side of said chart bearing a visual target pattern suitable for the left eye; wherein means for selectively actuating said central test stimulus is a test stimuli-bearing disc which is sandwiched between the two sides of said double-sided chart, and wherein a window is disposed in the central area of said chart through which the various test stimuli on said disc can be viewed.

18. A device as claimed in claim 17 wherein a notch is formed in the upper margin of said chart so as to expose a portion of said disc, said disc being rotatable in either direction by appropriate movement of a finger or other means located at the exposed edge of said disc.

19. A device as claimed in claim 17 wherein said disc is removably attached to said chart whereby different discs are interchangeable.

20. A device as claimed in claim 1 wherein the fixation targets are substantially regularly and successively arranged in a generally spiral configuration around the central test stimulus.

21. Apparatus as claimed in claim 20 wherein the fixation targets are arranged in a distorted spiral pattern in positions which are substantially equi-sensitive with respect to the stimulus.

22. Apparatus as claimed in claim 1 wherein said visual target has printed thereon a faint grid identifying said plurality of spaced individual fixation targets in the visual field.

23. A device as claimed in claim 1 wherein the visual target comprises a hand-held chart having printed thereon about sixty fixation targets identified by sequential numbers.

24. A device as claimed in claim 23 wherein said target numbers are linked by lines for assistance of patients in finding the next number.

25. A device as claimed in claim 23 wherein said target numbers are distributed in a substantially regular fashion at intervals of 4 degrees radially and 30 degrees meridionally.

26. A device as claimed in claim 1 which comprises a chart bearing said visual target pattern wherein an eye occluder is attached by means of a spiral hinge to a right side-arm; said side-arm being hingedly attached to a side of said chart.

27. A method of conducting examination of the visual field of a subject or patient by examining one eye at a time using a test chart comprising a visual target pattern with a plurality of spaced individual fixation targets and a test stimulus, said method comprising the steps of, (a) positioning the test chart at a desired distance from the subject, (b) occluding the eye not being examined, (c) causing the eye under examination to focus on a selected one of the fixation targets, (d) whilst said eye is so focused, making the test stimulus visible and invisible;

(e) recording whether the subject has observed the test stimulus (f) causing the eye under examination to move to a new fixation target according to a desired sequence;

(g) repeating steps (c) to (f) a number of times to create a map of subject responses to allow assessment of the visual field.

28. A method of conducting examination of the visual field of a subject or patient by examining one eye at a time using a test chart comprising a visual target pattern with a plurality of spaced individual fixation targets and a test stimulus, said method comprising the steps of:

(a) positioning the device at a desired distance from the subject;

(b) occluding the eye not being examined;

(c) causing the eye under examination to focus on a selected one of the fixation targets;

(d) while said eye is so focused, making the test stimulus visible and invisible;

(e) recording whether the subject has observed the test stimulus;

(f) causing the eye under examination to move to a new fixation target according to a desired sequence; and (g) repeating steps (c) and (f) a number of times to create a map of subject responses to allow assessment of the visual field.

29. A device for use in the examination of the visual field of a subject, the device comprising:

a generally planar surface defining a central aperture;

a central test stimulus which, in use of the device, may be viewable through said central aperture; and a moveable element which is moveable relative to said surface;

said surface having thereon a visual target pattern comprising a plurality of spaced individual fixation targets disposed in a predetermined configuration around said central aperture, and across substantially the whole of said visual target pattern, each individual fixation target incorporating sequence indicating means so as to define a visually discernible predetermined sequence for fixing the eye of the subject, in use of the device, on selected individual fixation targets, whereby movement of said moveable element selectively actuates said central test stimulus such that said central test stimulus can be made visible or invisible to the subject under test.

30. A device for use in the examination of the visual field of a subject, comprising:

a generally planar surface defining a central aperture;

a moveable element which is moveable relative to the surface;

a visual target pattern formed on the surface and including a plurality of spaced individual fixation targets disposed in a predetermined configuration around the central aperture; and at least one central test stimulus selectively viewable through the aperture, a predetermined movement of the moveable element changing the appearance of the central test stimulus.

31. The device of claim 30, wherein said at least one central test stimulus is formed on the moveable element.

32. The device of claim 30, and further comprising a plurality of central test stimuli including first and second central test stimuli visually different from each other and selectively viewable through the aperture, a predetermined movement of the moveable element substituting the second central test stimulus for the first central test stimulus in the central aperture.

33. The device of claim 30, wherein a predetermined movement of the moveable element causes said at least one central test stimulus to disappear.

* * * * *